US012336733B2

(12) United States Patent
Wang

(10) Patent No.: US 12,336,733 B2
(45) Date of Patent: Jun. 24, 2025

(54) PUNCTURE SUPPORT

(71) Applicant: SUZHOU LEAPMED HEALTHCARE CORPORATION, Suzhou (CN)

(72) Inventor: Qin Wang, Suzhou (CN)

(73) Assignee: SUZHOU LEAPMED HEALTHCARE CORPORATION, Suzhou (CN)

( * ) Notice: Subject to any disclaimer, the term of this patent is extended or adjusted under 35 U.S.C. 154(b) by 964 days.

(21) Appl. No.: 17/419,200

(22) PCT Filed: Dec. 27, 2018

(86) PCT No.: PCT/CN2018/124319
§ 371 (c)(1),
(2) Date: Jun. 28, 2021

(87) PCT Pub. No.: WO2020/133054
PCT Pub. Date: Jul. 2, 2020

(65) Prior Publication Data
US 2022/0142674 A1    May 12, 2022

(51) Int. Cl.
*A61B 17/34* (2006.01)
(52) U.S. Cl.
CPC ...... *A61B 17/3496* (2013.01); *A61B 17/3403* (2013.01); *A61B 2017/3413* (2013.01)
(58) Field of Classification Search
CPC ............ A61B 17/3496; A61B 17/3403; A61B 2017/3413; A61B 8/4209; A61B 8/4218; A61B 8/4227; A61B 8/4236
See application file for complete search history.

(56) References Cited

U.S. PATENT DOCUMENTS

| 5,738,401 A * | 4/1998 | Fan ...................... A45F 5/1046 294/171 |
| 6,368,280 B1 | 4/2002 | Cermak et al. |
| 6,447,190 B1 * | 9/2002 | Kwitek .................. A63B 53/14 401/6 |

(Continued)

FOREIGN PATENT DOCUMENTS

| CN | 102639182 A | 8/2012 |
| WO | 2011047066 A2 | 4/2011 |

*Primary Examiner* — Ashley L Fishback
(74) *Attorney, Agent, or Firm* — Sean S. Swidler; Swidler Law Group, LLC

(57) ABSTRACT

The present invention provides a puncture support, including a support body and a soft support coating covering the outside of the support body, wherein a needle insertion channel is provided inside the support body. During use, the puncture support is fixedly connected to an ultrasonic probe by using the hard support body, and the soft support coating attached to the support body is in contact with a human body. Because the support coating is made of a soft material, people feel soft with reduced foreign body sensation when in contact with the support coating. In addition, the support body is made of a hard material, so that the puncture support can be firmly installed, ensuring safety. Therefore, the puncture support can be firmly and reliably installed like an existing puncture support, and also increases the comfort level of the product by taking user feelings into account.

4 Claims, 1 Drawing Sheet

(56) References Cited

U.S. PATENT DOCUMENTS

| | | | | |
|---|---|---|---|---|
| 6,779,937 | B1 * | 8/2004 | Lombardi | A45D 40/205 |
| | | | | 401/6 |
| 6,968,599 | B2 * | 11/2005 | Blauer | A45C 13/26 |
| | | | | 81/177.1 |
| 7,334,298 | B2 * | 2/2008 | Willat | B25G 1/10 |
| | | | | 16/431 |
| 2003/0061715 | A1 * | 4/2003 | Heck | A01G 3/02 |
| | | | | 30/186 |
| 2011/0061249 | A1 * | 3/2011 | Ma | B25G 1/105 |
| | | | | 30/340 |
| 2014/0083969 | A1 * | 3/2014 | Porter | D04C 3/48 |
| | | | | 156/149 |
| 2014/0348564 | A1 * | 11/2014 | Vleisides | B43K 23/008 |
| | | | | 401/88 |
| 2016/0331468 | A1 * | 11/2016 | Lee | A61B 17/00234 |
| 2016/0380417 | A1 * | 12/2016 | Yamamoto | B60R 16/0215 |
| | | | | 174/68.3 |

* cited by examiner

PUNCTURE SUPPORT

TECHNICAL FIELD

The present invention relates to the fields of B-mode ultrasound intervention, and in particular, to a puncture support.

BACKGROUND

In clinical diagnosis and treatment using B-mode ultrasound intervention, puncture supports are required. Currently, all puncture supports on the market are generally categorized into three types by material: reusable stainless-steel puncture supports; disposable puncture supports made of a hard polymer material; and disposable puncture supports made of a mixture of a hard polymer material and a metal material. The materials of the foregoing puncture supports have one thing in common: they are all hard materials. During clinical use, a B-mode ultrasound probe equipped with a puncture support needs to be squeezed against and moved back and forth on a patient to check a lesion tissue and perform an intervention operation. The hard-material puncture supports can be installed firmly and reliably, but their disadvantage is also obvious: the hard materials are in direct contact with a body surface or cavity of the patient during use, increasing patient's discomfort, fear, and pain during examination and treatment.

SUMMARY

A main objective of the present invention is to provide a puncture support, including a hard support body and a soft support coating covering the outside of the support body. The support body provides firm support, positioning, and connection. The soft support coating is in direct contact with a patient's body, increasing the patient's comfort and reducing pain during examination or an operation.

To achieve the foregoing objective, the present invention provides the following technical solution.

A puncture support is provided, including a support body made of a hard material, where the outside of the support body is covered with a soft support coating.

Optionally, a needle insertion channel is provided inside the support body.

Optionally, the support body is manufactured through an injection molding process or a machine molding process.

Optionally, the soft support coating is manufactured through an overmolding process, an adhesive bonding process, a thermal bonding process, or an ultrasonic welding process.

Optionally, a material of the soft support coating is TPE, TPR, PVC, or silica gel.

Optionally, the support body has a guiding portion at the front end and a positioning portion at the rear end.

Optionally, the guiding portion has a needle exit hole, the positioning portion has a needle entrance hole, and the needle insertion channel extends from the needle entrance hole to the needle exit hole.

Optionally, the soft support coating is provided with a through hole at a location corresponding to the needle exit hole and a notch at a location corresponding to the needle entrance hole.

Optionally, the positioning portion includes two positioning rings arranged symmetrically.

Optionally, the support body has an arc-shaped cross section.

Structurally, the puncture support according to the present invention includes the support body and the soft support coating covering the outside of the support body. The hard support body provides support fixation and connection fixation with reliable strength. The soft support coating is in direct contact with a patient's body, increasing the patient's comfort and reducing pain and fear when the puncture support is used for the patient during examination or an operation. In addition, the support body is manufactured through a mature injection molding process with low costs. The soft support coating can cover a fin and a sharp corner formed in injection molding of the support body, avoiding injury to the patient.

BRIEF DESCRIPTION OF DRAWINGS

The drawings are used for better understanding of the present invention, and do not constitute improper limitation on the present invention.

1. soft support coating, 2. support body, and 21. needle insertion channel.

DESCRIPTION OF EMBODIMENTS

The following clearly and completely describes the technical solution in the embodiments of the present invention with reference to the accompanying drawings in the embodiments of the present invention. Apparently, the described embodiments are merely some but not all of the embodiments of the present invention. Based on the embodiments of the present invention, all other embodiments obtained by a person of ordinary skill in the art fall within the protection scope of the present invention.

Figure 1:
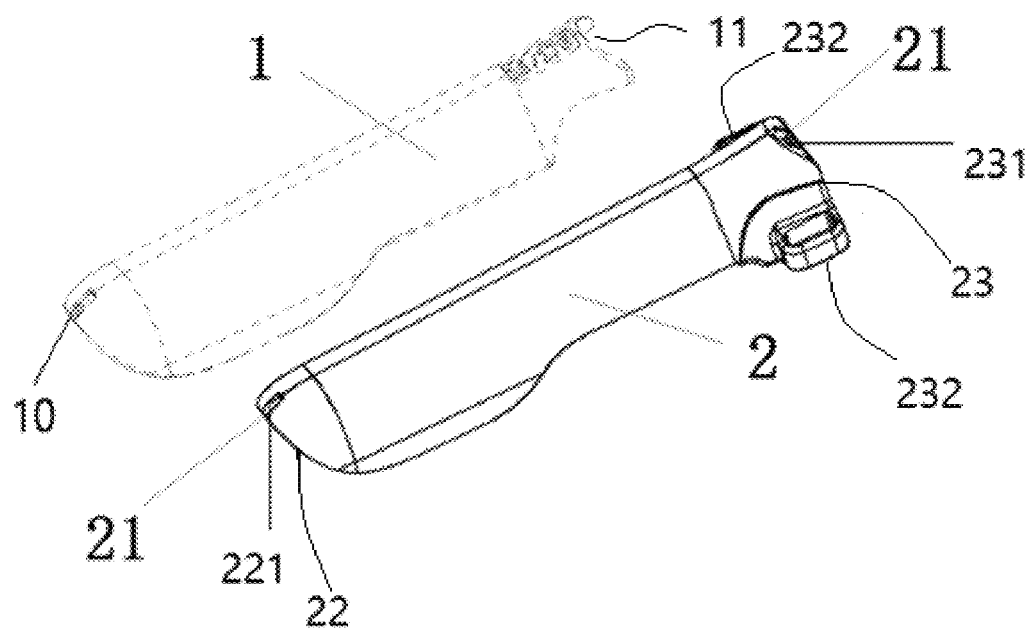
FIG. 1 is a schematic diagram of a disassembled puncture support according to the present invention.
Figure 2:
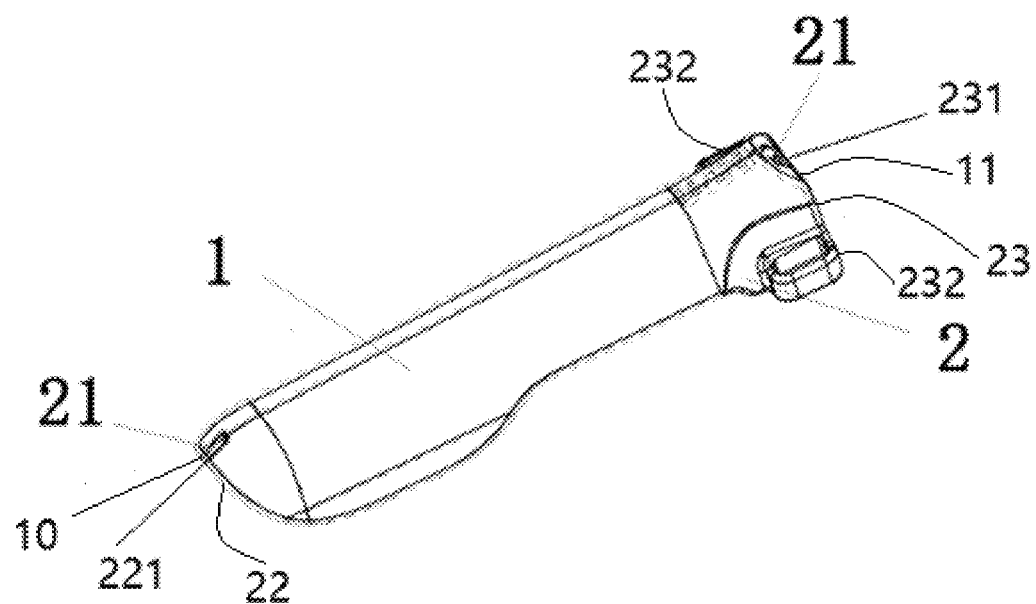
FIG. 2 is a schematic diagram of an assembled puncture support according to the present invention.

As shown in specific embodiments in FIG. 1 and FIG. 2, a puncture support includes a support body 2 made of a hard material and a soft support coating 1 (indicated by dashed lines in the figures) covering the outside of the support body 2. A needle insertion channel 21 is provided inside the support body 2.

A material of the soft support coating 1 may be TPE (thermoplastic elastomer), TPR (thermoplastic rubber), PVC (polyvinyl chloride), or silica gel. The support body 2 is manufactured through an injection molding process. The process is mature and not costly. The soft support coating 1 is manufactured through an overmolding process. With the overmolding process, a fin and a sharp corner formed in injection molding of the support body can be covered to avoid injury to a patient. Alternatively, a binding layer may be disposed between the support body 2 and the soft support coating 1. The binding layer fastens and connects the support body 2 and the soft support coating 1. The support body 2 has a guiding portion 22 at the front end and a positioning portion 23 at the rear end. The guiding portion 22 has a needle exit hole 221 and the positioning portion 23 has a needle entrance hole 231. The needle insertion channel 21 extends from the needle entrance hole 231 to the needle exit hole 221. The soft support coating 1 is provided with a through hole 10 at a location corresponding to the needle exit hole 221 and a notch 11 at a location corresponding to the needle entrance hole 231. The positioning portion 23 includes two positioning rings 232 arranged symmetrically. The support body 2 has an arc-shaped cross section (a plane corresponding to the cross section is perpendicular to the needle insertion channel), allowing easy access to a cavity of the patient. The support body 2 is provided with transverse and longitudinal stiffeners on the rear side. The support body 2 is of a symmetrical structure.

The puncture support includes two parts: a hard material part (the support body) and a soft material part (the soft support coating). The two parts are firmly attached together through an overmolding process or other special processes, to form a new puncture support having a soft surface and a firm and reliable internal structure. During use, the puncture support is fixedly connected to an ultrasonic probe by using the support body, and the soft support coating attached to the support body is in contact with a human body. Because the support coating is made of a soft material, people feel soft with reduced foreign body sensation when in contact with the support coating. In addition, the support coating covers factors that may cause body discomfort, for example, a blur on the surface of the support body. In addition, the support body is made of a hard material, so that the puncture support can be firmly installed, ensuring safety. Therefore, the puncture support can be firmly and reliably installed like an existing puncture support, and also significantly increases the comfort level of the product by taking user feelings into account.

The foregoing embodiments do not constitute any limitation on the protection scope of the present invention. A person skilled in the art should understand that, various modifications, combinations, sub-combinations, and substitutions may be made depending on a design requirement and other factors. Any modification, equivalent replacement, and improvement made without departing from the spirit and principle of the present invention shall fall within the protection scope of the present invention.

The invention claimed is:

1. A puncture support, comprising a support body made of a hard material, wherein the outside of the support body is covered with a soft support coating, the soft support coating is fastened and connected to the support body by means of a binding layer, the support body has a guiding portion at the front end and a positioning portion at the rear end, the guiding portion has a needle exit hole, the positioning portion has a needle entrance hole, the needle insertion channel extends from the needle entrance hole to the needle exit hole, and the soft support coating is provided with a through hole at a location corresponding to the needle exit hole and a notch at a location corresponding to the needle entrance hole.

2. The puncture support according to claim 1, wherein a needle insertion channel is provided inside the support body.

3. The puncture support according to claim 1, wherein a material of the soft support coating is TPE, TPR, PVC, or silica gel.

4. The puncture support according to claim 1, wherein the support body has an arc-shaped cross section.

* * * * *